United States Patent [19]

Holmes et al.

[11] Patent Number: 4,462,814
[45] Date of Patent: Jul. 31, 1984

[54] DISTILLATIVE SEPARATIONS OF GAS MIXTURES CONTAINING METHANE, CARBON DIOXIDE AND OTHER COMPONENTS

[75] Inventors: Arthur S. Holmes, Shrewsbury; James M. Ryan, Weston, both of Mass.

[73] Assignee: Koch Process Systems, Inc., Westboro, Mass.

[21] Appl. No.: 476,520

[22] Filed: Mar. 18, 1983

Related U.S. Application Data

[63] Continuation of Ser. No. 308,164, Oct. 2, 1981, abandoned, which is a continuation-in-part of Ser. No. 94,226, Nov. 14, 1979, Pat. No. 4,318,723, and Ser. No. 131,416, Mar. 18, 1980, abandoned, and Ser. No. 143,099, Apr. 23, 1980, Pat. No. 4,293,322, and Ser. No. 306,419, Sep. 28, 1981, Pat. No. 4,350,511.

[51] Int. Cl.³ .............................................. F25J 3/04
[52] U.S. Cl. ............................................ 62/17; 55/68; 62/20; 62/28
[58] Field of Search .......................... 62/17, 20, 23–28; 55/68, 73; 423/220, 226

[56] References Cited

U.S. PATENT DOCUMENTS

| | | | |
|---|---|---|---|
| 3,983,711 | 10/1976 | Solomon | 62/28 |
| 4,097,250 | 6/1978 | Pagani et al. | 62/17 |
| 4,115,086 | 9/1978 | Jordon | 62/28 |
| 4,185,978 | 1/1980 | McGalliard | 62/28 |
| 4,311,495 | 1/1982 | Styring | 62/28 |

Primary Examiner—Frank Sever
Attorney, Agent, or Firm—Richard P. Crowley

[57] ABSTRACT

Distillative separations of hydrocarbon feed mixtures containing at least methane and carbon dioxide, as well as other components, such as ethane, higher hydrocarbons, and hydrogen sulfide are disclosed. In the separations described, methane is preferably separated from an acid gas under conditions of composition, temperature and pressure which would normally produce acid gas solids. Acid gas solids are prevented by adding a liquid solids-preventing agent into this distillation column. A second distillation column is subsequently employed to further separate the feed gas mixture. The second distillation column is operated under conditions which an azeotrope would normally form between the light hydrocarbon and carbon dioxide, which azeotrope would limit the carbon dioxide overhead composition. The azeotrope is prevented by introducing an agent for preventing azeotrope formation. Alternatively, the second distillation column may be operated to separate carbon dioxide from hydrogen sulfide. In this case, a liquid agent is added to the second distillation column to increase the relative volatility of carbon dioxide to hydrogen sulfide. All liquid agents preferably comprise a $C_3$–$C_6$ alkane, such as butane, or a mixture of such alkanes.

32 Claims, 2 Drawing Figures

DISTILLATIVE SEPARATIONS OF GAS MIXTURES CONTAINING METHANE, CARBON DIOXIDE AND OTHER COMPONENTS

RELATED APPLICATIONS

This is a continuation of application Ser. No. 308,164, filed Oct. 2, 1981 (now abandoned), which is a continuation-in-part of our prior applications: Ser. No. 94,226, filed Nov. 14, 1979, now U.S. Pat. No. 4,318,723; Ser. No. 131,416, filed Mar. 18, 1980, now abandoned; Ser. No. 143,099, filed Apr. 23, 1980, now U.S. Pat. No. 4,293,322; and, Ser. No. 306,419, filed Sept. 28, 1981, now U.S. Pat. No. 4,350,511; the teachings of which applications are hereby incorporated by reference herein.

DESCRIPTION

Background Art

Gas streams obtained from natural gas wells often contain undesirably high amounts of carbon dioxide, hydrogen sulfide, or other acid gases, in addition to methane and other hydrocarbons having good heating value. In such cases, it is customary to remove as much carbon dioxide, hydrogen sulfide, or other acid gas as is practical.

Additionally, efforts are recently being made to achieve enhanced oil recovery from existing wells. For example, carbon dioxide-containing gases can be injected into oil wells to achieve enhanced oil or gas recovery. Gas streams recovered by such efforts typically contain methane, ethane and higher hydrocarbons having good heat content, but also contain undesirable amounts of carbon dioxide, and in some cases hydrogen sulfide or other acid gases. Thus, it is usually necessary to remove carbon dioxide, and often other acid gas components such as hydrogen sulfide, from such gas streams to produce pipeline quality gas.

Distillative separations offer great potential for removing carbon dioxide, hydrogen sulfide and other undesirable components. Based solely upon relative volatilities, for example, it is theoretically possible to perform distillative separations of: (1) methane from carbon dioxide; (2) carbon dioxide from ethane; and (3) carbon dioxide from hydrogen sulfide. In practice, however, factors other than relative volatility come into play and these additional factors often interfere with achieving effective distillative separations under practical operating conditions.

For example, the problems which have been encountered in attempting to separate significant quantities of carbon dioxide from methane by distillative means are described in our copending application, Ser. No. 94,226. In this copending application, it is pointed out that the formation of carbon dioxide solids could interfere with such distillative separations, but this problem could be overcome by introducing an agent which would prevent carbon dioxide solids formation.

Furthermore, attempts to distillatively separate light hydrocarbons, such as ethane, from carbon dioxide were often limited because an azeotrope could form in a distillation column and this azeotrope could limit the overhead concentration of carbon dioxide which could be achieved. This type of problem is described in our copending application Ser. No. 131,416, together with a solution to this problem. The solution described in our copending application relates to the introduction into the distillation column of a liquid agent which serves to keep the relative volatility of carbon dioxide to ethane above 1 so that a limiting azeotrope is not formed.

Some gas mixtures also contain undesirable amounts of hydrogen sulfide. Efforts to separate carbon dioxide and hydrogen sulfide by distillative techniques often encountered another problem due to the low relative volatility of carbon dioxide to hydrogen sulfide at high carbon dioxide concentrations. Our copending application, Ser. No. 143,099, describes such a problem and sets forth a solution involving the addition of an agent to increase the relative volatility between these materials.

In each of the aforementioned distillative separations, it was found that non-polar liquids could be successfully employed as the added agent in each case. Thus, individual $C_3$-$C_6$ alkanes, for example, were suitable, as were mixtures of hydrocarbons such as those mixtures found in NGL's.

DISCLOSURE OF THE INVENTION

This invention relates to distillative separations of hydrocarbon feed mixtures containing at least methane and carbon dioxide, as well as other components. These other components can include ethane, higher hydrocarbons, nitrogen, hydrogen sulfide, etc.

In these separations, methane is separated from acid gases such as carbon dioxide in a first distillation column. The overhead product of this first distillation column is a methane-enriched gas which can be substantially free of acid gases. The bottoms product can be substantially free of methane. Unlike certain other prior distillative separations, this first distillation column can be operated at temperatures, compositions and pressures which would normally produce acid gas solids in the tower.

The term "solids potential zone" is employed because, as explained below, although conditions in the tower are such that the acid gas solids would normally occur, thus interferring with the desired separation, the process described herein prevents actual solids formation from occurring in the first distillation column. In order to avoid actual acid gas solids formation in the solids potential zone, an agent for preventing acid gas solids is added to the first distillation column so that it is present throughout the solids potential zone. This agent can be an external additive, or in the alternative, can be one or more recycled components from the bottoms product taken from the first distillation column. The solids-preventing agent is added in a sufficient quantity to prevent carbon dioxide or other acid gas components from forming solids in the solids potential zone of the column, thereby allowing a more complete distillative separation of methane from acid gas components to be achieved in a first distillation column.

A second distillation column is subsequently employed to separate further the feed gas mixture. If the feed contained ethane or other light hydrocarbons, then the bottoms product from the first column can be passed to a second column. This bottoms product from the first distillation column, which is enriched in carbon dioxide, is introduced into a second distillation column, wherein it is separated into an overhead product enriched in carbon dioxide and a bottoms product enriched in light hydrocarbon. This is achieved by adding to the second distillation column an agent which prevents formation of an azeotrope between carbon dioxide and the light hydrocarbon which would limit the overhead concentration of carbon dioxide which can be removed from the column. For example, an agent which prevents azeotrope formation between carbon dioxide and ethane can be employed in this distillative separation so that an overhead stream having significantly more than about two-thirds carbon dioxide, the limit when an azeotrope forms, can be achieved.

If hydrogen sulfide is present in the initial feed mixture, the bottoms product from the first distillation column, which is enriched in both carbon dioxide and hydrogen sulfide, can be introduced into a second column to separate carbon dioxide from hydrogen sulfide. In this case, the second column is operated under conditions which are sufficient to produce an overhead stream enriched in carbon dioxide and a bottoms stream enriched in hydrogen sulfide. An agent for increasing the volatility of carbon dioxide to hydrogen sulfide is added to this distillation column to cause a more complete separation.

The method disclosed herein results in the ability to carry out distillative separations of certain components which are undesirable in gas mixtures obtained from natural gas wells, in enhanced oil recovery efforts, or otherwise. As described, such distillative separations can be employed to produce very efficient separations of methane, ethane, carbon dioxide, and hydrogen sulfide, from the feed gas.

A particular advantage of these separations is that the same material can be employed as an agent for preventing carbon dioxide solids formation in the first distillation column, for preventing azeotrope formation in a second distillation column for separating carbon dioxide from light hydrocarbons, or for effecting a more complete separation of hydrogen sulfide from carbon dioxide in a second distillation column. Further, this material can be a material present in the initial feed mixture which can be subsequently separated, such as from bottoms product withdrawn from the second distillation column, and subsequently recycled to the first or second distillation columns employed in the separations described herein.

BRIEF DESCRIPTIONS OF THE DRAWINGS

BEST MODE OF CARRYING OUT THE INVENTION

This invention will now be further described in more specific detail with regard to the Figures. Unless otherwise specified, all percentages are mole percentages.

Figure 1:
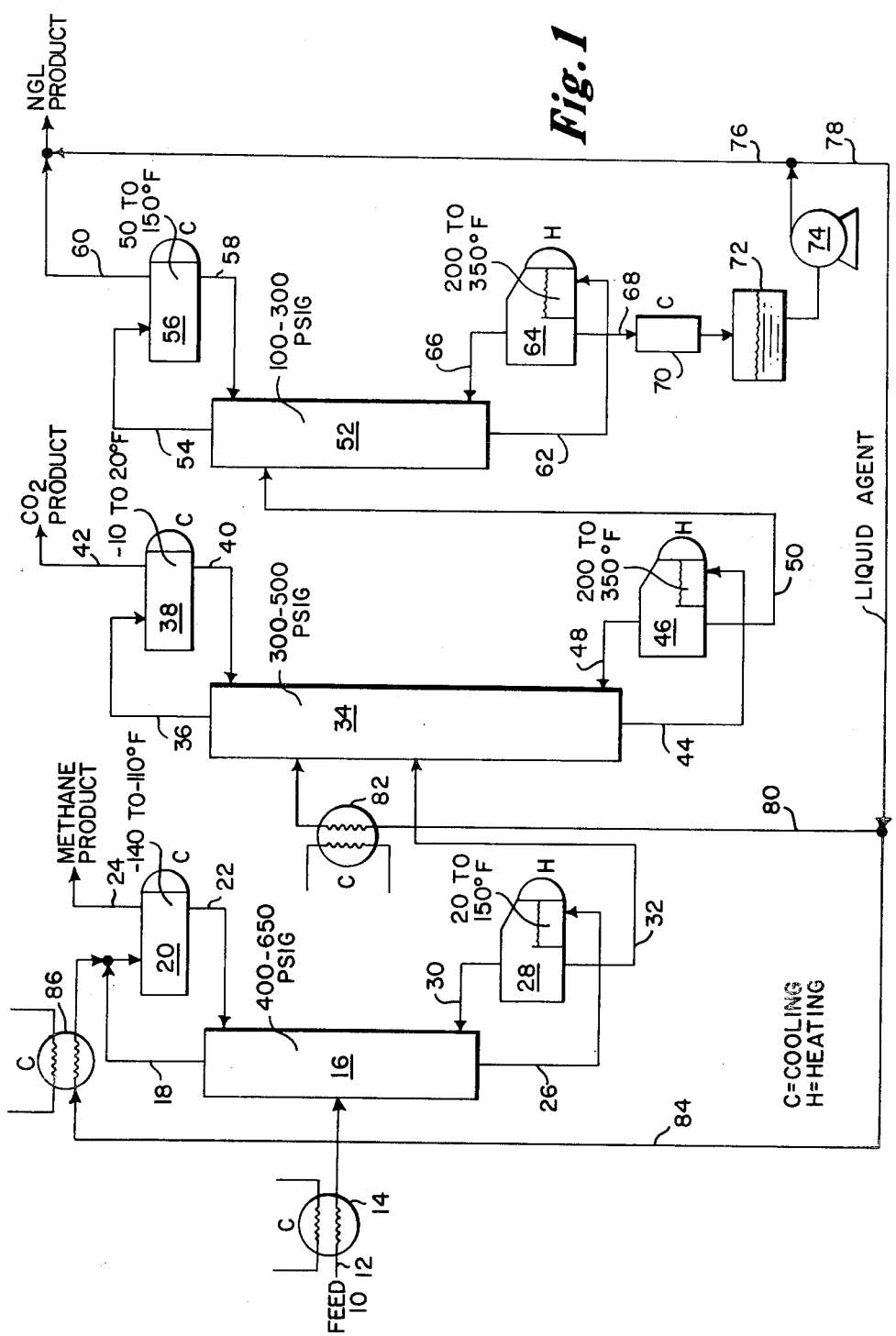
FIG. 1 is a schematic flow diagram illustrating distillative separations of methane from carbon dioxide and carbon dioxide from ethane.

Distillative separations of a feed gas containing methane, carbon dioxide, ethane and other components are illustrated in FIG. 1. Typical operating temperatures are indicated at various locations on FIG. 1 and areas at which cooling or heating are employed are designated by the letters "C", and "H", respectively. Additionally, typical flow rates and compositions at various points in the system illustrated in FIG. 1, based upon a flow rate of 2,000 lb. moles per hour of feed having the specified composition, are given in Table I:

TABLE I

|  | Feed | | Methane Product | | $CO_2$ Product | | NGL Product | |
|---|---|---|---|---|---|---|---|---|
|  | mph | % | mph | % | mph | % | mph | % |
| $N_2$ | 98 | 4.9 | 98 | 16.3 | 0 |  | 0 |  |
| $C_1$ | 514 | 25.7 | 491 | 81.64 | 19 | 1.8 | 4 | .1 |
| $CO_2$ | 1000 | 50.0 | 10 | 1.7 | 987 | 94.3 | 3 | .3 |
| $C_2$ | 158 | 7.9 | 0 |  | 40 | 3.8 | 118 | 33.6 |
| $H_2S$ | 3.6 | 1.8 | ~0 | ~1 ppm | 0.1 | 0.01 | 3.5 | .0 |
| $C_3$ | 132 | 6.6 | 0.2 | .03 | 1. | .09 | 130.8 | 37.1 |
| $C_4$ | 62 | 31 | 1.5 | .25 | 0 |  | 60.5 | .7.2 |
| $C_5$ | 26 | 1.3 | .5 | .08 | 0 |  | 25.5 | .3 |
| $C_6+$ | 6.4 | .32 | — | — |  | 6.4 | 1.8 |  |
| Total | 2000.0 | 100.0 | 601.2 | 100.0 | 1047.1 | 100.0 | 351.7 | 100.0 | mph = lb. moles per hour
% = mole percent

Feed gas 10, typically previously dried, is passed in flow line 12 through precooler 14 and into a first or demethanizer distillation column 16. Distillation column 16 contains a number of vapor-liquid contact devices, such as trays or packing, with the exact number of contact stages depending upon the required operating conditions. Dried, precooled feed 10 is introduced typically at approximately the mid-point of column 16.

Overhead, enriched in methane, is withdrawn from column 16 in overhead line 18 and passed to condenser 20. Condenser 20 is supplied with cooling, as indicated, sufficient to condense at least a portion of the overhead gas, which condensate is subsequently returned, via line 22, to column 16 as reflux. The balance of overhead gas is withdrawn in line 24 as methane product.

Bottoms exits from column 16 through flow line 26 and is introduced into reboiler 28 which is heated. Reboiled vapors are returned to distillation column 16 in line 30. Bottoms product is directed in line 32 into a second distillation column 34. Thus, the feed to column 34 is enriched in both carbon dioxide and ethane compared to the feed to column 16.

Overhead gas is withdrawn from column 34 in overhead line 36 and at least partially condensed in condenser 38. Condensed liquid flows through flow line 40 into the upper portion of column 34 to serve as reflux. The remaining portion of withdrawn overhead gas is taken from condenser 38 in flow line 42 as $CO_2$ product.

Bottoms is withdrawn from column 34 in line 44 and passed to reboiler 46 which is heated. A portion of the bottoms is vaporized and returned in line 48 to column 34. The balance of bottoms is directed in flow line 50 into a third distillation column 52. This feed to column 52 is enriched in ethane and any higher hydrocarbons present in the original feed 10.

Overhead, enriched in lighter hydrocarbons such as ethane and propane, is withdrawn from column 52 in flow line 54. This overhead is passed to condenser 56, provided with cooling, to condense a portion thereof which is directed through line 58 back to the upper portion of column 52 wherein it serves as reflux. The remaining portion of overhead gas is withdrawn in line 60 for ultimate use in forming an NGL product.

Bottoms enriched in butane is withdrawn from column 52 in flow line 62 and is directed to reboiler 64 which is heated. Reboiled vapors are returned in line 66 to column 52. The balance of heated bottoms is withdrawn in line 68 and directed to cooler 70. Cooled bottoms product accumulates in surge tank 72 from which it can be pumped by pump 74 to a number of locations.

For example, a first portion of bottoms product can be directed by pump 74 through flow line 76 for combination with overhead gas flowing in line 60 to produce NGL product.

The remaining portion of bottoms product from column 52 can be directed by pump 74 through flow line 78 to either or both of distillation columns 16 or 34 as non-polar liquid agent. As shown, a portion of the recycled bottoms liquid can be directed by flow line 80 through cooler 82 and into the upper portion of distillation column 34 in accordance with the principles set forth in our copending application, Ser. No. 131,416.

Similarly, a portion of recycled bottoms liquid can be directed in flow line 84 through cooler 86 and into condenser 20 according to the principles set forth in our copending application, Ser. No. 94,226.

The net result of the distillative separations are as follows. As can be seen from Table I, the overhead methane product from column 16 contains a total of 97.9% methane plus nitrogen and only about 1.7% carbon dioxide. In column 34, a carbon dioxide overhead product is produced having 94.3% carbon dioxide and only a small amount of hydrocarbons. Column 52 produces an NGL product, as well as a butane-enriched liquid which can be recycled as agent for preventing carbon dioxide solids formation in column 16 as well as agent for preventing formation of an azeotrope between carbon dioxide and ethane in column 34.

Figure 2:
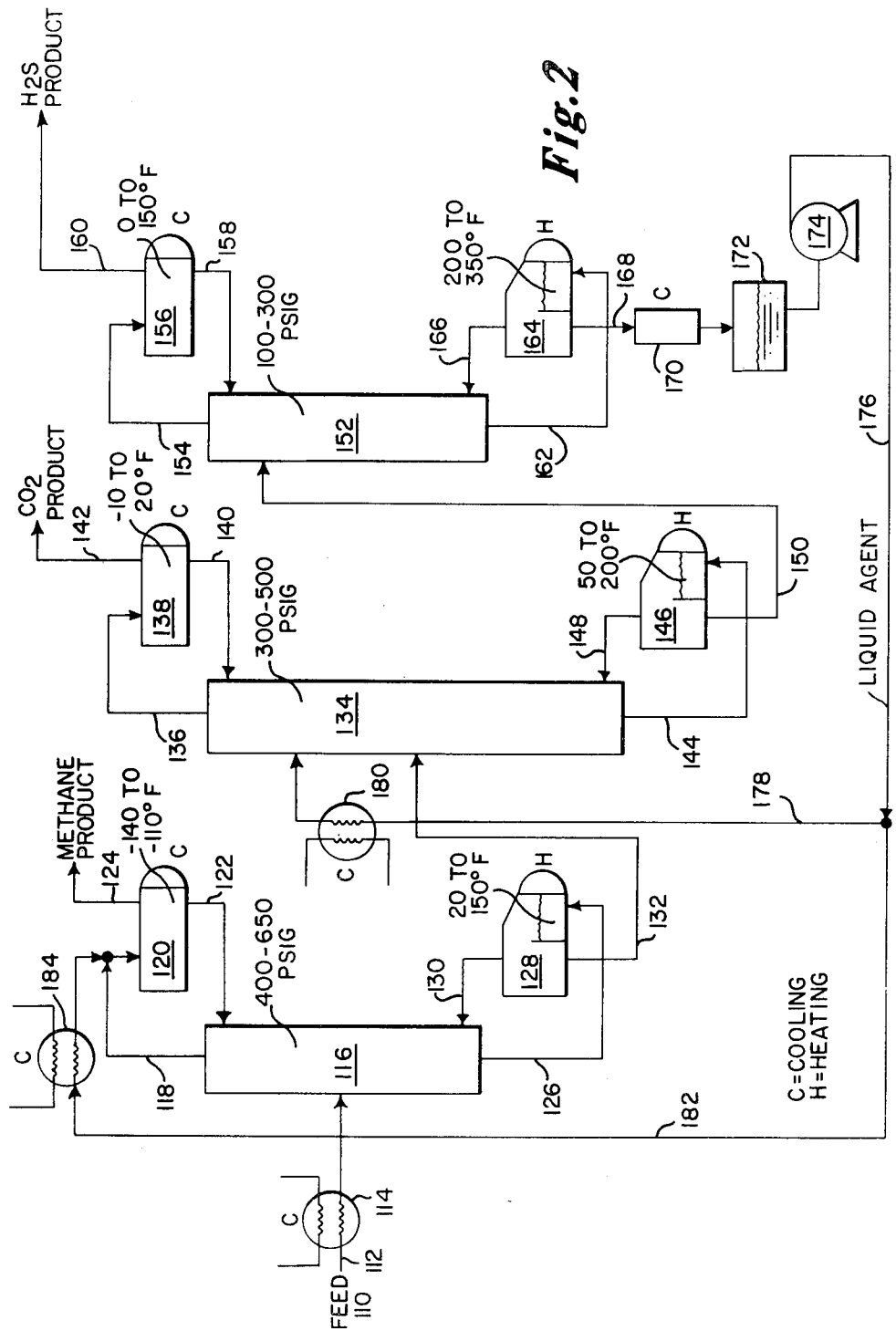
FIG. 2 is a schematic flow diagram illustrating distillative separations of methane from carbon dioxide and carbon dioxide from hydrogen sulfide.

Distillative separations of a feed gas containing relatively high amounts of carbon dioxide and hydrogen sulfide, but little ethane, are illustrated in FIG. 2. In a manner similar to FIG. 1, typical operating pressures and temperatures are indicated on FIG. 2 as are the points of use of cooling or heating. The flow rates and mole percentages of the various components in the feed at various points in the overall process are as follows, based upon a flow rate of 10,000 lb. moles per hour of feed:

flows through line 122 back to the upper portion of column 116 to serve as reflux. The balance of overhead gas is withdrawn from condenser 120 in flow line 124 as methane product.

Bottoms is withdrawn from column 116 in line 126 and directed to reboiler 128 which is heated. Reboiled vapors are returned in line 130 to the bottom portion of column 116. The remaining portion of bottoms is directed in line 132 to second distillation column 134 which serves to separate carbon dioxide from hydrogen sulfide. The feed entering column 134 through line 132 is enriched in both carbon dioxide and hydrogen sulfide compared to feed 110.

Overhead is withdrawn from column 134 in flow line 136 and directed to condenser 138 which is provided with sufficient cooling to condense at least a portion thereof. Condensed liquid flows into line 140 to the upper portion of column 134 to serve as reflux. The balance of overhead from column 134 is withdrawn from condenser 138 in flow line 142 as carbon dioxide product.

Bottoms from column 134 is withdrawn in line 144 and directed to reboiler 146 which is heated. Reboiled vapors are returned in line 148 to the bottom portion of column 134 and the remaining portion of bottoms from column 134 is directed in line 150 to distillation column 152. Distillation column 152 is operated to distillatively separate hydrogen sulfide from a bottoms product.

Overhead is withdrawn from column 152 in line 154 and directed to condenser 156 which is provided with sufficient cooling to condense at least a portion thereof. Condensed liquid is returned in line 158 to the upper portion of column 152 as reflux. The balance of overhead from column 152 is withdrawn in flow line 160 as hydrogen sulfide product.

Bottoms from column 152 is withdrawn in flow line 162 and is directed to reboiler 164 which is heated. Reboiled vapors are returned in line 166 to column 152. The remaining portion of withdrawn bottoms is directed via line 168 to cooler 170 to provide a liquid bottoms product in surge tank 172. Liquid bottoms product can be pumped from tank 172 by pump 174 and directed to column 134 via flow lines 176 and 178 and heat exchanger 180. Therein, it serves to increase the relative volatility of carbon dioxide to hydrogen sulfide, as described in our copending application, Ser. No. 143,099.

Similarly, liquid bottoms product flowing in line 176 can be directed through line 182 to cooler 184 and back to condenser 120. Thus, it is returned into column 116 in the liquid reflux and can serve in column 116 to prevent

TABLE II

|  | Feed | | Methane Product | | $CO_2$ Product | | $H_2S$ Product | |
| --- | --- | --- | --- | --- | --- | --- | --- | --- |
|  | mph | % | mph | % | mph | % | mph | % |
| $N_2$ | 50 | 0.5 | 50 | 2.0 | 0 | — | 0 | — |
| $C_1$ | 2650 | 26.5 | 2500 | 97.8 | 150 | 2.1 | 0 | — |
| $CO_2$ | 7185 | 71.85 | ~.0 | 50 ppm | 7085 | 97.5 | 100 | 55.6 |
| $C_2$ | 50 | .5 | 0 |  | 25 | .3 | 25 | 13.9 |
| $H_2S$ | 50 | .5 | ~0 | <1 ppm | 0.3 | 40 ppm | 49.7 | 27.7 |
| $C_3+$ | 15 | .15 | 4 | .2 | 6 | .1 | 5. | 2.8 |
| Total | 10000 | 100.0 | 2554. | 100.0 | 7266.3 | 100.0 | 179.7 | 100.0 |

As illustrated, feed gas 110 is passed in line 112 to precooler 114 and then introduced into distillation column 116 at about the mid-point thereof. Overhead is withdrawn in line 118 and directed to condenser 120 which is provided with cooling sufficient to condense at least a portion of the overhead gas. Condensed liquid carbon dioxide solids formation according to the principles of our copending application, Ser. No. 94,226.

The net results of the separations illustrated in FIG. 2 is an overhead methane product containing 99.8% methane and nitrogen and less than 1 ppm $H_2S$. The overhead carbon dioxide product from the second column contains 97.5% $CO_2$ and significantly less than 100 ppm $H_2S$. The $H_2S$ product is significantly enriched in $H_2S$ compared to the feed gas and contains a $CO_2/H_2S$ mole ratio of approximately 2/1, which is desirable, for example, in feeds for a Claus plant.

Although the feed to columns 34 and 134 in FIGS. 1 and 2, respectively, have been described in terms of originating from columns 16 and 116, which can be operated under conditions to create a $CO_2$ solids potential zone, this is not necessary. More generally, columns 16 and 116 can be run under any conditions sufficient to separate feed gas containing methane and carbon dioxide into a methane-enriched overhead gas and a carbon dioxide-enriched bottoms.

It should also be recognized, of course, that the overhead product from the second distillation column 34 in FIG. 1 could optionally be directed to a column, such as column 134 in FIG. 2, to perform a distillative separation of carbon dioxide from hydrogen sulfide, if desired or necessary. Similarly, the overhead product from second distillation column 134 in FIG. 2 could optionally be directed to a column to separate carbon dioxide from light hydrocarbons, such as column 34 in FIG. 1, if it contained significant amounts of light hydrocarbons, such as ethane.

As pointed out above, an advantage to the distillative separations described herein is that the agent introduced into the demethanizer column to prevent acid gas solids, the agent introduced to prevent azeotrope formation between carbon dioxide and light hydrocarbons, and the agent intoduced into a column to increase the relative volatility of carbon dioxide to hydrogen sulfide, can be the same liquid agent. Of course, although illustrated as being the same agent, it need not be the same agent and a different material may be selected for the agent introduced into each of the columns.

In general, any material or mixture of materials which are non-polar liquids, such as ethane, propane, n- or i-butane, n- or i-pentane, hexane and other alkanes, can be employed as suitable agents in the separations described herein. Certain materials, such as $C_3$–$C_6$ alkanes, are typically present in feed gases and are relatively easy to separate and recycle, and may be preferred in some cases for these reasons.

In addition to these preferred materials, there are other classes of materials which may be suitable. For example, other hydrocarbons, halogenated hydrocarbons, such as fluoro-chloromethane compounds; ammonia; sulfur dioxide; etc., and mixtures thereof, may be suitable. Those skilled in the art will know, or be able to ascertain using no more than routine experimentation and the teachings set forth in our copending applications, Ser. Nos. 94,226, 131,416, 143,099, other suitable liquid agents for use with the distillative separations described herein.

The amount of agent added will be dependent upon factors such as the composition of the feed, operating pressure, throughput of the column, desired purity of the overhead product, etc. Such factors can be taken into account by those skilled in the art by determining the operative amounts for any given separation using no more than routine experimentation together with the teachings of the above-referenced copending applications.

In general, the amount of the liquid additive agent to be employed in columns such as column 34 may vary, such as, for example, from about above 10% mole and above in the liquids in the column below the point where the agent is added, preferably, 20% and above in the column, and particularly 25% mole and above. The liquid additive agent may range in concentration in one embodiment from about 30 to 50% mole in the liquids in the main zone of the column and be present in about 70 to 90% mole in the hydrocarbon-enriched bottoms product.

It has also been found, in certain cases, that better results are achieved if the total amount of agent added is distributed in more than one location within the column. This is another factor which those skilled in the art can determine using the teachings of this invention together with teachings of our copending applications and routine experimentation.

Industrial Applicability

This invention is useful in distillative separations of feed gas mixtures containing methane, carbon dioxide and other components such as hydrogen sulfide and ethane or higher hydrocarbons.

Equivalents

Those skilled in the art will recognize, or be able to determine using no more than routine experimentation, other equivalents to the specific embodiments described herein. These and other equivalents are intended to be covered by the claims appended hereto.

We claim:

1. A distillative separation of a hydrocarbon feed mixture containing at least methane and one other light hydrocarbon and an acid gas capable of forming an azeotrope with said light hydrocarbon, comprising:
   a. introducing said feed mixture into a first distillation column;
   b. operating said first distillation column at conditions of pressure, temperature and composition sufficient to produce a methane-enriched overhead and a bottoms containing light hydrocarbon and enriched in acid gas based upon the methane and acid gas present in said feed mixture, said conditions of temperature, pressure and composition creating a solids potential zone for said acid gas within the distillation column where said acid gas would normally form solids;
   c. introducing a liquid solids-preventing agent into the solids potential zone in the upper portion of said first column in sufficient amount to eliminate acid gas solids formation in the solids potential zone;
   d. withdrawing said methane-enriched overhead;
   e. withdrawing the liquid solids-preventing agent with said bottoms enriched in light hydrocarbon and said acid gas;
   f. introducing said bottoms from said first distillation column into a second distillation column;
   g. operating said second distillation column at conditions of pressure, temperature and composition sufficient to produce an acid gas-enriched overhead stream and a light hydrocarbon-enriched bottoms based upon the light hydrocarbon and acid gas present in bottoms from the first distillation column introduced into said second distillation column, said conditions of pressure, temperature and composition also being sufficient normally for the formation of an acid gas/light hydrocarbon azeotrope which would limit the concentration of acid gas in said overhead stream to the azeotropic concentration, based upon a binary mixture of said acid gas and said light hydrocarbon;

h. introducing into the upper portion of said distillation column and above the point of introduction of bottoms from said first distillation column a liquid agent sufficient to provide a relative volatility of greater than 1 of said acid gas to said light hydrocarbon at or below the point of introduction of the liquid agent to provide an acid gas-enriched overhead stream having an acid gas concentration greater than the azeotropic concentration of a binary mixture of said acid gas and said light hydrocarbon;

i. withdrawing said acid gas-enriched overhead from the second distillation column; and, j. withdrawing said light hydrocarbon-enriched bottoms from the second distillation column.

2. A distillative separation of claim 1 wherein said acid gas comprises carbon dioxide.

3. A distillative separation of claim 2 wherein said light hydrocarbon comprises ethane.

4. A distillative separation of claims 1, 2 or 3 wherein said liquid solids-preventing agent comprises a non-polar liquid miscible with methane.

5. A distillative separation of claim 4 wherein said liquid solids-preventing agent comprises ethane, propane, butane, pentane or mixtures thereof.

6. A distillative separation of claims 1, 2 or 3 wherein said liquid agent sufficient to provide a relative volatility of greater than 1 for said acid gas and said light hydrocarbon comprises a non-polar liquid.

7. A distillative separation of claim 6 wherein said liquid solids-preventing agent comprises a non-polar liquid miscible with methane.

8. A method of claims 1 or 3 wherein both of said liquid solids-preventing agent and said liquid agent for maintaining the relative volatility of greater than 1 of said acid gas to said light hydrocarbon comprise butane.

9. A distillative separation of claims 1 or 3 wherein said liquid agent sufficient to provide a relative volatility of greater than 1 for said acid gas and said light hydrocarbon is introduced into said second distillation column in a concentration of above about 10 mole percent in the liquids in the column below the point of introduction.

10. A distillative separation of claims 1 or 3 in which said liquid agent sufficient to provide a relative volatility of greater than 1 for said acid gas and said light hydrocarbon is introduced into said second distillation column in a concentration of about 30 to 50 mole percent in the liquids in said column below the point of introduction and about 70 to 90 mole percent in bottoms from said column.

11. A distillative separation of claim 1 wherein said liquid solids-preventing agent is separated from bottoms product withdrawn from said first distillation column.

12. A distillative separation of claims 1 or 11 wherein said liquid agent for providing a relative volatility of greater than 1 of said acid gas to said light hydrocarbon is separated from bottoms product withdrawn from said second distillation column.

13. A distillative separation of claim 1 wherein said feed mixture additionally contains hydrogen sulfide and the overhead product from said second distillation column is subsequently introduced into a distillation column operated to separate carbon dioxide from hydrogen sulfide.

14. A distillative separation of a hydrocarbon feed mixture containing at least methane, carbon dioxide and hydrogen sulfide, comprising:

a. introducing said feed mixture into a first distillation column;

b. operating said first distillation column at conditions of pressure, temperature and composition sufficient to produce a methane-enriched overhead and a bottoms containing hydrogen sulfide and enriched in carbon dioxide based upon the methane and carbon dioxide present in said feed mixture, said conditions of pressure, temperature and composition creating a solids potential zone for carbon dioxide within said distillation column where said carbon dioxide would normally form solids;

c. introducing a liquid solids-preventing agent into the solids potential zone in the upper portion of said first column in sufficient amount to eliminate carbon dioxide solids formation in the solids potential zone;

d. withdrawing from the first distillation column said methane-enriched overhead;

e. withdrawing the liquid solids-preventing agent with said bottoms enriched in carbon dioxide and containing the hydrogen sulfide;

f. introducing said bottoms from the first distillation column into a second distillation column;

g. operating said second distillation column at conditions of pressure, temperature and composition sufficient to produce a carbon dioxide-enriched overhead stream and a hydrogen sulfide-enriched bottoms stream based upon the carbon dioxide and hydrogen sulfide present in said bottoms from the first distillation column;

h. introducing into said second distillation column at a location above the feed point thereto an agent for increasing the relative volatility of carbon dioxide to hydrogen sulfide;

i. withdrawing from the second distillation column said carbon dioxide-enriched overhead; and, j. withdrawing from the second distillation column said bottoms enriched in hydrogen sulfide.

15. A distillative separation of claim 14 wherein said agent for raising the relative volatility of carbon dioxide to hydrogen sulfide comprise a $C_3-C_6$ alkane, a mixture of $C_3-C_6$ alkanes, $SO_2$ or $SO_3$.

16. A distillative separation of claim 15 wherein said liquid agent is miscible in the liquid phase at all points in said second distillation column.

17. A distillative separation of claim 16 wherein said miscible liquid agent comprises butane.

18. A distillative separation of claims 14, 15, 16 or 17 wherein said liquid solids-preventing agent comprises a non-polar liquid miscible with methane.

19. A distillative separation of claim 18 wherein said liquid solids-preventing agent comprises ethane, propane, butane, pentane or mixtures thereof.

20. A distillative separation of claim 18 wherein said liquid solids-preventing agent comprises butane.

21. A distillative separation of claim 18 wherein said agent for increasing the relative volatility of carbon dioxide to hydrogen sulfide is separated from bottoms from said second distillation column and recycled thereto.

22. A distillative separation of claim 21 wherein said liquid solids-preventing agent is separated from bottoms from said first distillation column and recycled thereto.

23. A distillative separation of claim 14 wherein said feed additionally contains significant amounts of light hydrocarbon and said overhead product from said second distillation column is introduced into an additional distillation column for separation of carbon dioxide from said additional light hydrocarbon.

24. A distillative separation of a hydrocarbon feed mixture containing at least methane and one other light hydrocarbon and an acid gas capable of forming an azeotrope with said light hydrocarbon, comprising:
   a. introducing said feed mixture into a first distillation column;
   b. operating said first distillation column under conditions sufficient to produce a methane-enriched overhead and a bottoms containing the light hydrocarbon and enriched in acid gas based upon the methane and acid gas present in said feed mixture;
   c. withdrawing from the first distillation column said methane-enriched overhead;
   d. withdrawing from the first distillation column said bottoms enriched in acid gas;
   e. introducing said bottoms from the first distillation column into a second distillation column;
   f. operating said second distillation column at conditions of pressure, temperature and composition sufficient to produce an acid gas-enriched overhead stream and a light hydrocarbon-enriched bottoms based upon the acid gas and light hydrocarbon present in bottoms from said first distillation column, said conditions of temperature, pressure and composition also being sufficient normally for the formation of an acid gas/light hydrocarbon azeotrope which would limit the concentration of acid gas in said overhead stream to the azeotropic concentration, based upon a binary mixture of said acid gas and light hydrocarbon;
   g. introducing into the upper portion of said distillation column and above the point of introduction of bottoms from said first distillation column a liquid agent in an amount of greater than about 20 mole percent of the liquid agent based on the moles of liquids in the column at or below the point of introduction of the liquid agent and sufficient to provide a relative volatility of greater than 1 of said acid gas to said light hydrocarbon at or below the point of introduction of the liquid agent to provide an acid gas-enriched overhead stream having an acid gas concentration greater than the azeotropic concentration of a binary mixture of said acid gas and said light hydrocarbon;
   h. withdrawing said acid gas-enriched overhead from the second distillation column; and
   i. withdrawing said light hydrocarbon-enriched bottoms from the second distillation column.

25. A distillative separation of claim 24 wherein said acid gas comprises carbon dioxide.

26. A distillative separation of claim 25 wherein said light hydrocarbon comprises ethane.

27. A distillative separation of claim 26 wherein said agent sufficient to provide a relative volatility of greater than 1 for said acid gas and light hydrocarbon comprises a non-polar liquid.

28. A distillative separation of claim 27 wherein said non-polar liquid comprises a $C_3$–$C_6$ alkane.

29. A distillative separation of claim 28 wherein said $C_3$–$C_6$ alkane is separated from bottoms from said second distillation column and recycled thereto.

30. A distillative separation of a hydrocarbon feed mixture containing at least methane, carbon dioxide and hydrogen sulfide, comprising:
   a. introducing said feed mixture into a first distillation column;
   b. operating said first distillation column at conditions sufficient to produce a methane-enriched overhead and a bottoms containing hydrogen sulfide and enriched in carbon dioxide based upon the methane and carbon dioxide present in said feed mixture;
   c. withdrawing from the first distillation column said methane-enriched overhead;
   d. withdrawing from the first distillation column said bottoms enriched in carbon dioxide;
   e. introducing said bottoms from the first distillation column into a second distillation column;
   f. operating said second distillation column at conditions of pressure, temperature and composition sufficient to produce a carbon dioxide-enriched overhead stream and a hydrogen sulfide-enriched bottoms stream based upon the carbon dioxide and hydrogen sulfide present in said bottoms from the first distillation column;
   g. introducing into said second distillation column at a location above the feed point thereof an agent for increasing the relative volatility of carbon dioxide to hydrogen sulfide, said agent being selected from a $C_3$–$C_6$ alkane, $SO_2$, $SO_3$, and mixtures thereof;
   h. withdrawing from the second distillation column said carbon dioxide-enriched overhead; and
   i. withdrawing from the second distillation column said bottoms enriched in hydrogen sulfide.

31. A distillative separation of a hydrocarbon feed mixture containing methane, carbon dioxide, ethane, and at least one $C_3$–$C_6$ alkane, comprising:
   a. precooling said feed mixture;
   b. introducing said precooled feed mixture into a first distillation column;
   c. operating said first distillation column at conditions of pressure, temperature and composition sufficient to produce a methane-enriched overhead and a bottoms containing ethane and $C_3$–$C_6$ alkane and enriched in carbon dioxide based upon the methane and carbon dioxide present in the feed mixture, said conditions of pressure, temperature and composition creating a solids potential zone for said carbon dioxide within said first distillation column where carbon dioxide solids would normally form;
   d. introducing a liquid solids-preventing agent comprising one or more $C_3$–$C_6$ alkanes into the solids potential zone in the upper portion of said first distillation column in sufficient amount to eliminate carbon dioxide solids formation in said solids potential zone;
   e. withdrawing said methane-enriched overhead;
   f. condensing a portion of said methane-enriched overhead and directing said condensed portion back to said first distillation column as reflux;
   g. withdrawing the balance of said methane-enriched overhead as methane product,
   h. withdrawing said bottoms enriched in carbon dioxide;
   i. reboiling a portion of said bottoms and redirecting it to said first distillation column;
   j. introducing the balance of bottoms from said first distillation column into a second distillation column;

k. operating said second distillation column at conditions of pressure, temperature and composition sufficient to produce a carbon dioxide-enriched overhead stream and an ethane-enriched bottoms based upon the carbon dioxide and ethane in bottoms from said first distillation column, said conditions of pressure, temperature and composition also being sufficient normally for the formation of a carbon dioxide/ethane azeotrope which would limit the concentration of carbon dioxide in said overhead to the azeotropic concentration, based upon a binary mixture of said acid gas and said light hydrocarbon;

l. introducing into the upper portion of said second distillation and above the point of introduction of bottoms from said first distillation column a liquid agent sufficient to provide a relative volatility of greater than 1 of said acid gas to said light hydrocarbon at or below the point of introduction of said liquid agent to provide a carbon dioxide-enriched overhead stream having a carbon dioxide concentration greater than the azeotropic concentration of a binary mixture of carbon dioxide and ethane, said agent comprising one or more $C_3$–$C_6$ alkanes;

m. withdrawing said carbon dioxide-enriched overhead from said second distillation column;

n. condensing a portion of said carbon dioxide-enriched overhead and redirecting it to said second distillation column as reflux;

o. withdrawing the balance of said carbon dioxide-enriched overhead as a carbon dioxide product;

p. withdrawing said ethane-enriched bottoms from the second distillation column;

q. reboiling a portion of said ethane-enriched bottoms and redirecting said portion back to said second distillation column;

r. introducing the balance of said ethane-enriched bottoms from the second distillation column into a third distillation column;

s. operating said third distillation column under conditions sufficient to produce a bottoms product enriched in a $C_3$–$C_6$ alkane based upon the feed thereto; and t. recycling said bottoms product enriched in a $C_3$–$C_6$ alkane from said third distillation column to both of said first distillation column as liquid solids-preventing agent and to said second distillation column as liquid agent sufficient to provide a relative volatility of greater than 1 of said carbon dioxide to said ethane therein.

32. A distillation separation of a hydrocarbon feed mixture containing at least methane, carbon dioxide, hydrogen sulfide and a $C_3$–$C_6$ alkane, comprising:

a. precooling said feed mixture;

b. introducing said precooled feed mixture into a first distillation column;

c. operating said first distillation column at conditions of pressure, temperature and composition sufficient to produce a methane-enriched overhead and a bottoms containing hydrogen sulfide and $C_3$–$C_6$ alkane and enriched in carbon dioxide based upon the methane and carbon dioxide present in said feed mixture, said conditions of pressure, temperature and composition creating a solids potential zone for said carbon dioxide within said first distillation column where carbon dioxide solids would normally form;

d. introducing a liquid solids-preventing agent comprising one or more $C_3$–$C_6$ alkanes into the solids potential zone in the upper portion of said first distillation column in sufficient amount to eliminate carbon dioxide solids formation in said solids potential zone;

e. withdrawing said methane-enriched overhead;

f. condensing a portion of said methane-enriched overhead and directing said condensed portion back to said first distillation column as reflux;

g. withdrawing the balance of said methane-enriched overhead as methane product;

h. withdrawing said bottoms enriched in carbon dioxide;

i. reboiling a portion of said bottoms and redirecting it to said first distillation column;

j. introducing the balance of bottoms from said first distillation column into a second distillation column;

k. operating said second distillation column at conditions of pressure, temperature and composition sufficient to produce a carbon dioxide-enriched overhead stream and a bottoms stream containing $C_3$–$C_6$ alkane and enriched in hydrogen sulfide based upon the carbon dioxide and hydrogen sulfide present in bottoms from the first distillation column;

l. withdrawing said carbon dioxide-enriched overhead stream from said second distillation column;

m. condensing a portion of said carbon dioxide-enriched overhead and redirecting it to said second distillation column as reflux;

n. removing the balance of carbon dioxide-enriched overhead as carbon dioxide product;

o. withdrawing said bottoms enriched in hydrogen sulfide from said second distillation column;

p. reboiling a portion of said hydrogen sulfide-enriched bottoms product and directing said reboiled portion back to said distillation column;

q. introducing the balance of withdrawn hydrogen sulfide-enriched bottoms from said second distillation column into a third distillation column;

r. operating said third distillation column under conditions sufficient to produce an overhead enriched in hydrogen sulfide and a bottoms enriched in one or more $C_3$–$C_6$ alkanes based upon the hydrogen sulfide and $C_3$–$C_6$ alkanes present in feed thereto; and s. recycling bottoms from said third distillation column to both of said first distillation column as liquid solids-preventing agent and to said second distillation column as agent for raising the relative volatility of carbon dioxide to hydrogen sulfide therein.

* * * * *